United States Patent
Narang et al.

Patent Number: 5,091,502
Date of Patent: Feb. 25, 1992

[54] TETRAKETONE PORPHYRIN MONOMERS AND THE PORPHYRIN-BASED POLYMERS THEREOF

[75] Inventors: Subhash C. Narang, Redwood City; Susanna Ventura, Mountain View; Tilak R. Bhardwaj, Redwood City, all of Calif.

[73] Assignee: General Petrochemical Industries Ltd, Tokyo, Japan

[21] Appl. No.: 491,747

[22] Filed: Mar. 12, 1990

Related U.S. Application Data

[63] Continuation-in-part of Ser. No. 247,590, Sep. 23, 1988, Pat. No. 4,908,442.

[30] Foreign Application Priority Data

Sep. 22, 1989 [JP] Japan ................. 1-247849

[51] Int. Cl.⁵ .................................. C08G 12/00
[52] U.S. Cl. .................................. 528/229; 528/27; 528/125; 528/128; 528/226; 524/80; 524/404; 524/438; 524/440; 525/471
[58] Field of Search ............... 528/229, 125, 128, 226, 528/27; 524/404, 438, 440, 80; 525/471

[56] References Cited

U.S. PATENT DOCUMENTS 4,499,260  2/1985  Achar et al. ................. 528/229

Primary Examiner—Earl Nielsen
Assistant Examiner—Frederick Krass
Attorney, Agent, or Firm—Phillips, Moore, Lempio & Finley

[57] ABSTRACT

The present invention relates to a tetraketone of the structure

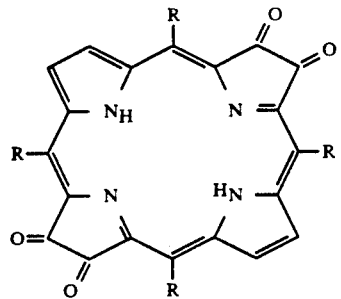

or

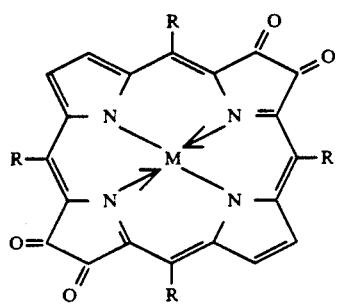

wherein M is a metal atom and R is selected from phenyl, alkyl substituted phenyl or halogen substituted phenyl. The process to prepare this tetraketone is disclosed. The present invention also relates to a process to produce the tetraketone structure(I). The present invention also relates to the novel polymer of the structure:

(Abstract continued on next page.)

and to the process to produce this novel polymer. R is as defined hereinabove, and Ar is a tetraamine substituted organic moiety having at least one aromatic ring. These polymers are useful as liquid crystals and in nonlinear optical devices.

25 Claims, 5 Drawing Sheets

PREPARATION OF 5, 10, 15, 20-TETRAPHENYLPORPHYRIN (H$_2$TPP)

PURIFICATION FROM CHLORIN BY REACTION WITH DDQ

DDQ =

IIa

FIG._4

β-PYRROLIC NITRATION

IIa

IIIa

FIG._5

PREPARATION OF LADDER-LIKE
METALLO-PORPHYRIN POLYMERS

1. COUPLING (POLYMER X)
2. TREATMENT WITH METAL SALT

POLYMER Xa

TETRAKETONE PORPHYRIN MONOMERS AND THE PORPHYRIN-BASED POLYMERS THEREOF

ORIGIN OF THE INVENTION

This application is a continuation-in-part of U.S. patent application Ser. No. 247,590, filed Sept. 23, 1988, which issued as U.S. Pat. No. 4,908,442, on Mar. 13, 1990, which is incorporated herein by reference in its entirety.

BACKGROUND OF THE INVENTION

1. Field of Invention

The present invention relates to the synthesis of novel tetraketone porphyrin monomers and the linear porphyrin polymers produced when these porphyrins are condensed with tetramines. These polymers have a number of uses including non-linear optical materials, electrochromic polymers, semiconductor and electrically conducting polymers and advanced structural materials.

2. Description of Related Art

M. J. Crossley and Paul L. Burn published in the *Journal of Chemical Society, Chemical Communications*, 1987, p. 39–40, the synthesis of rigidly bridged bis-porphyrin systems involving the 2:1 condensation of an alpha dione (17,18-dioxochlorine) with a tetra-amine.

M. J. Crossley published about July 15, 1988 in the Abstracts Booklet of the 196th Annual American Chemical Society Meeting to be held in Los Angeles on Sept. 26 to 31, 1988 (Abstract 60 (Inorganic Division)), showing only the structure of a linear ladder-type porphyrin polymer. No additional enabling experimental details were provided.

All reference articles or patents cited in this application are incorporated in their entirety herein by reference.

It is therefore desirable to produce a tetraketone porphyrin (metal) monomer, and the polymers obtained by the reaction with tetraamines or tetraamine hydrohalides. The present invention accomplishes these objectives.

SUMMARY OF THE INVENTION

The present invention relates to a tetraketoneporphyrin of the structure:

or

-continued wherein R is phenyl, alkyl substituted, or halogen substituted phenyl, M is any metal atom, preferably selected from copper, iron, nickel, cobalt or manganese.

In another aspect, the present invention relates to a process for the preparation of a tetraketone of the structure:

or wherein M an R are defined hereinabove, which process comprises:

(a) treating the chemical of the structure:

with an oxidizing agent to remove any dihydrochlorin impurity and produce compound II in at least 95% purity;

(b) contacting the compound II of step (a) with a metal salt to produce the metal porphyrin II(a):

(c) containing the compound II(a) with $N_2O_4$ to produce the dinitro-III(a) of the structure;

plus other isomers (d) contacting the dinitro compound III(a) of step (c) with concentrated sulfuric acid to product the dinitro demetallized compound III:

plus other isomers (e) reducing the dinitro-IV of step (d) with a reducing agent to produce the diamino-III of the structure:

plus other isomers (f) contacting the diamino-IV of step (e) with an oxidizing agent to produce the tetraketone of structure I.

In another aspect, the present invention relates to the aforementioned process, which further includes:

(g) contacting the compound of step (f) with a metal salt to produce a metal porphyrin of the structure I(a):

where M and R are as defined hereinabove.

In another aspect, the present invention relates to an electrically conductive polymer of the structure X:

wherein
M is a metal atom, preferably selected from copper, iron, cobalt, nickel, or manganese;
R is selected from phenyl, alkyl substituted phenyl, or halogen substituted phenyl; and
Ar is selected from the group consisting of:

when Q is oxygen, A is —(CH$_2$)$_m$—, —(CH$_2$CH(CH$_3$))$_m$—,

—(CF$_2$CF$_2$)$_m$—, or —(CF$_2$CF(CF$_3$))$_m$—; or when Q is a direct carbon-carbon bond, A is —(CH$_2$CH$_2$O)$_m$—, —(CH$_2$CH(CH$_3$)O)$_m$—, or —(SiR$_2$O)$_m$—; wherein R' is methyl, ethyl, propyl or butyl and m is 1 to 10,000, preferably 10 to 10,000.

In another aspect, the present invention relates to a process to produce a linear polymer of the structure:

wherein
 M is selected from any metal atom, preferably copper, iron, cobalt, nickel, or manganese;
 Ar is as defined hereinabove;
 R is selected from phenyl, alkyl substituted phenyl and halogen substituted phenyl, which process comprises:
 (a) contacting a tetraketone of structure I:

with a tetraamine or a tetraamine hydrohalide selected from the group of structures consisting of:

-continued

-continued wherein Q is oxygen (O), A is (—CH$_2$)$_m$—, —(CH$_2$CH(CH$_3$))$_m$—, —(OCF$_2$CF$_2$)$_m$—, or —(CF$_2$—CF(CF$_3$))$_m$—; or when Q is a direct carbon-carbon bond, A is —(CH$_2$CH$_2$O)$_m$—, —(CH$_2$CH(CH$_3$)O)$_m$—, or —(SiR'$_2$O)$_m$—, wherein R' is methyl, ethyl, propyl, or butyl and m is 1 to 10,000, preferably 10 to 10,000.

(b) maintaining the solution of step (a) for between about 0.1 to 6 days at about ambient temperature or higher and recovering the polymer of structure X.

DETAILED DESCRIPTION OF THE INVENTION AND PREFERRED EMBODIMENTS

Definitions:

As used herein:

"Metal(s)" refers to any atom of the Periodic Table having the properties of a metal. These include preferably all transition metals, actinides and lanthanides. More preferably copper, iron, cobalt, nickel or manganese are used. See *Porphyrins and Metalloporphyrins* by K. M. Smith Elsevier/North-Holland Biochemical Press 1976, which is incorporated herein by reference.

"Metal salt" refers to an organic or inorganic salt used to treat a dihydro-porphyrin structure to produce the corresponding metal porphyrin compound. Acetates and propionates are preferred.

Synthesis of the Tetraketoporphyrin Monomer

Referring to FIGS. 1 to 5, is described the synthetic route to obtain a tetraketoporphyrin monomer, Compound I, e.g., where R is phenyl.

Figure 2:
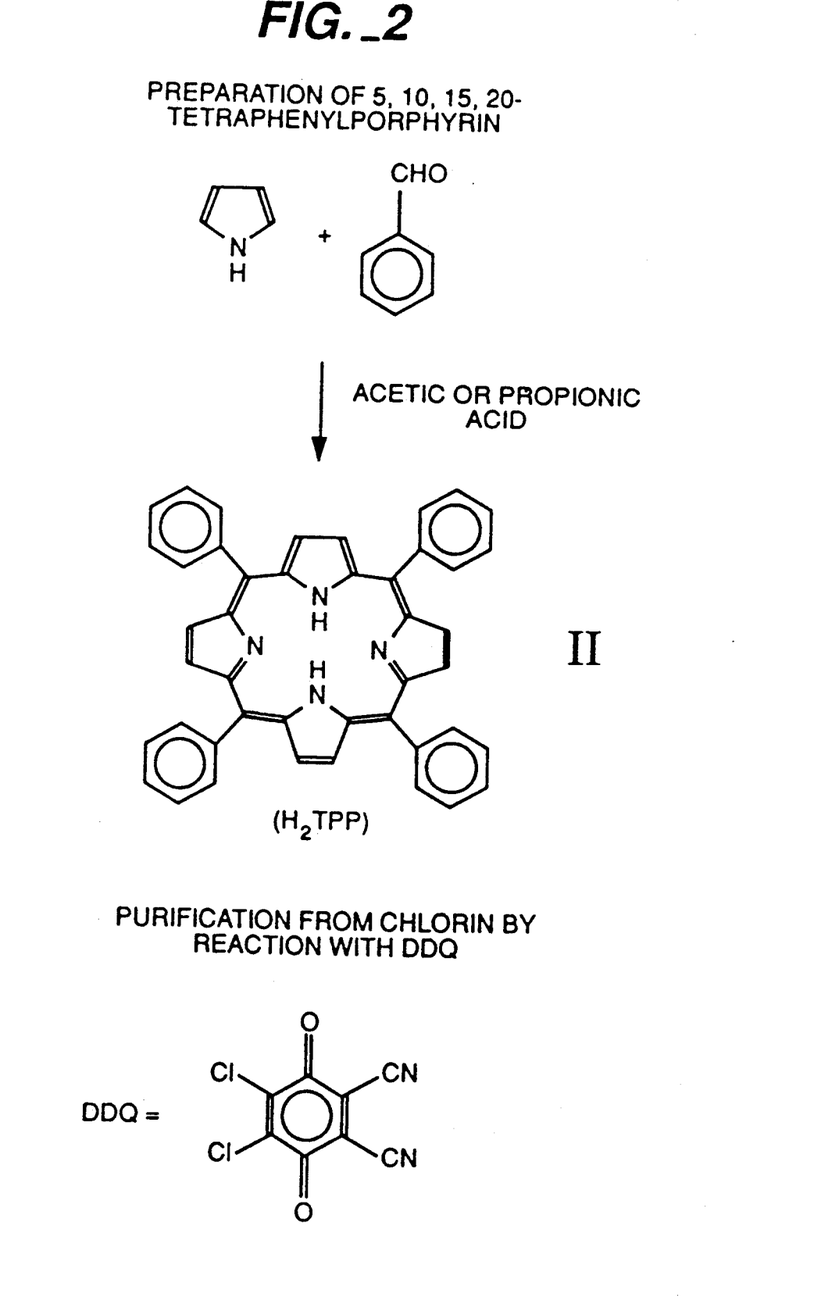
FIG. 2 shows a reaction for the synthesis and purification the starting material 5,10,15,20 tetraphenylporphyrin (II).

Tetraphenylporphyrin (Compound II): The preparation of Compound II is obtained according to the procedure reported by A. D. Adler, F. R. Longo, J. D. Finarelli, J. Goldmacher, J. Assour, and L. Korsakoff, *Journal of Organic Chemistry*, 32, 476 (1967), Which is incorporated herein by reference. Equimolar quantities of pyrrole and a benzaldehyde are combined using acetic acid or propionic acid.

Different porphyrin compounds are prepared by replacing the benzaldehyde with stoichiometrically equivalent amounts of 4-methylbenzaldehyde, 3,5-dimethylbenzaldehyde, 4-chlorobenzaldehyde, 4-methoxybenzaldehyde, and the like.

Figure 3:
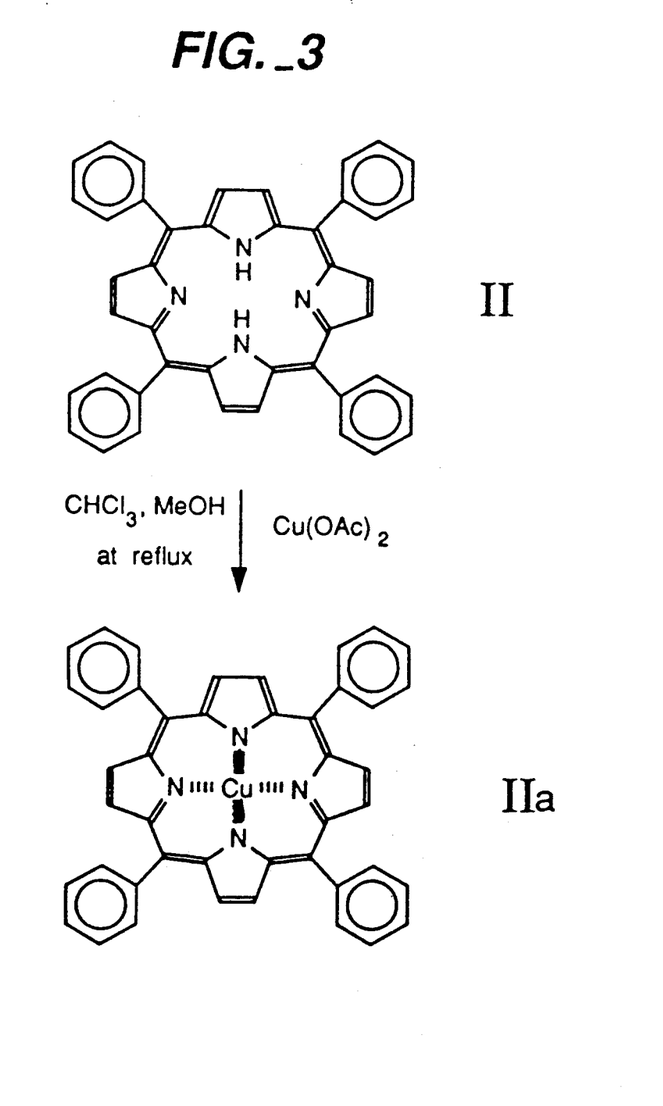
FIG. 3 shows a reaction for the synthesis of a copper (II) porphyrin intermediate (IIa).

Metal Tetraphenyl Porohyrin (IIa): Compound II is combined with a metal acetate, in a solvent of, for example, chloroform and methanol. The solution is heated at reflux for between about 15 and 30 min. After cooling, the solid product IIa is obtained by filtration. Different metal acetate reagents will produce different metal porphyrins. Preferred metals include, for example, copper, iron, nickel, cobalt, or manganese. Copper is more preferred.

Figure 4:
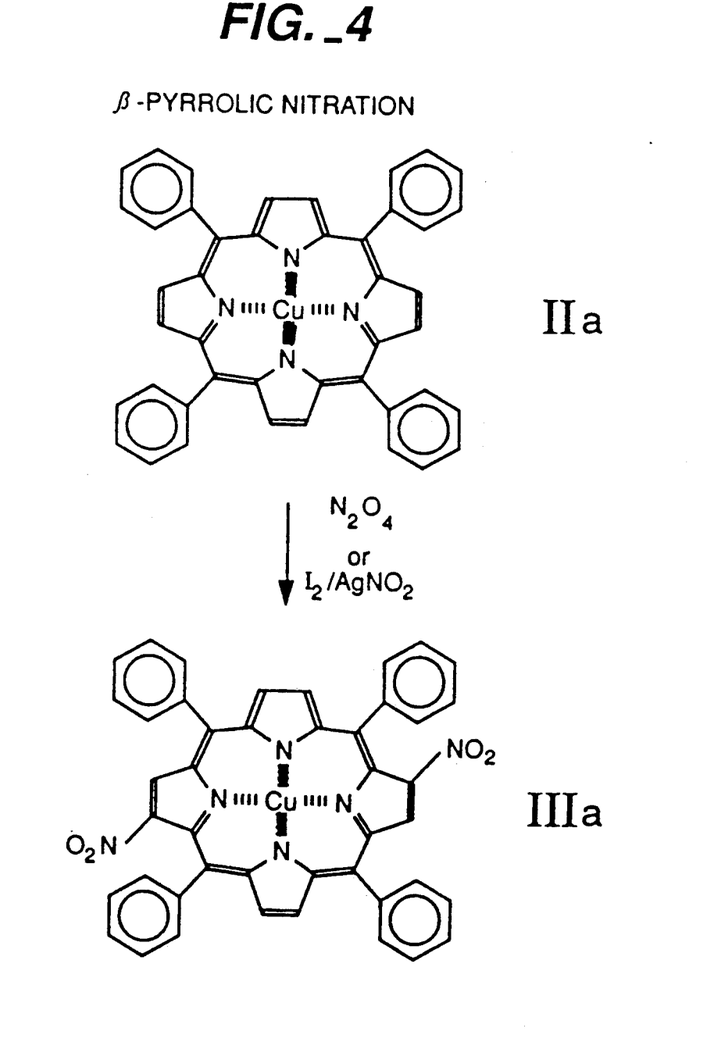
FIG. 4 shows a reaction for the synthesis of a dinitroporphyrin intermediate (IIIa).

Metal (II) Dinitrotetraphenylporphyrins and their Demetallation: Compound IIIa: The metal (IIa) porphyrin, Compound IIa, is dissolved in excess dipolar aprotic solvent, such as methylene chloride, chloroform or the like, in an inert atmosphere, such as nitrogen or argon. Solvent and a nitrating agent, such as dinitrogen tetraoxide are combined. The nitrating agent solution is slowly added to the methylene chloride solution of the porphyrin. Next, the crude product is contacted with excess concentrated sulfuric acid. The product is carefully poured onto ice/water and extracted. The solid product is Compound III. The infrared, mass and proton nuclear magnetic spectral data are consistent with the dinitroderivative attributes.

Figure 1:
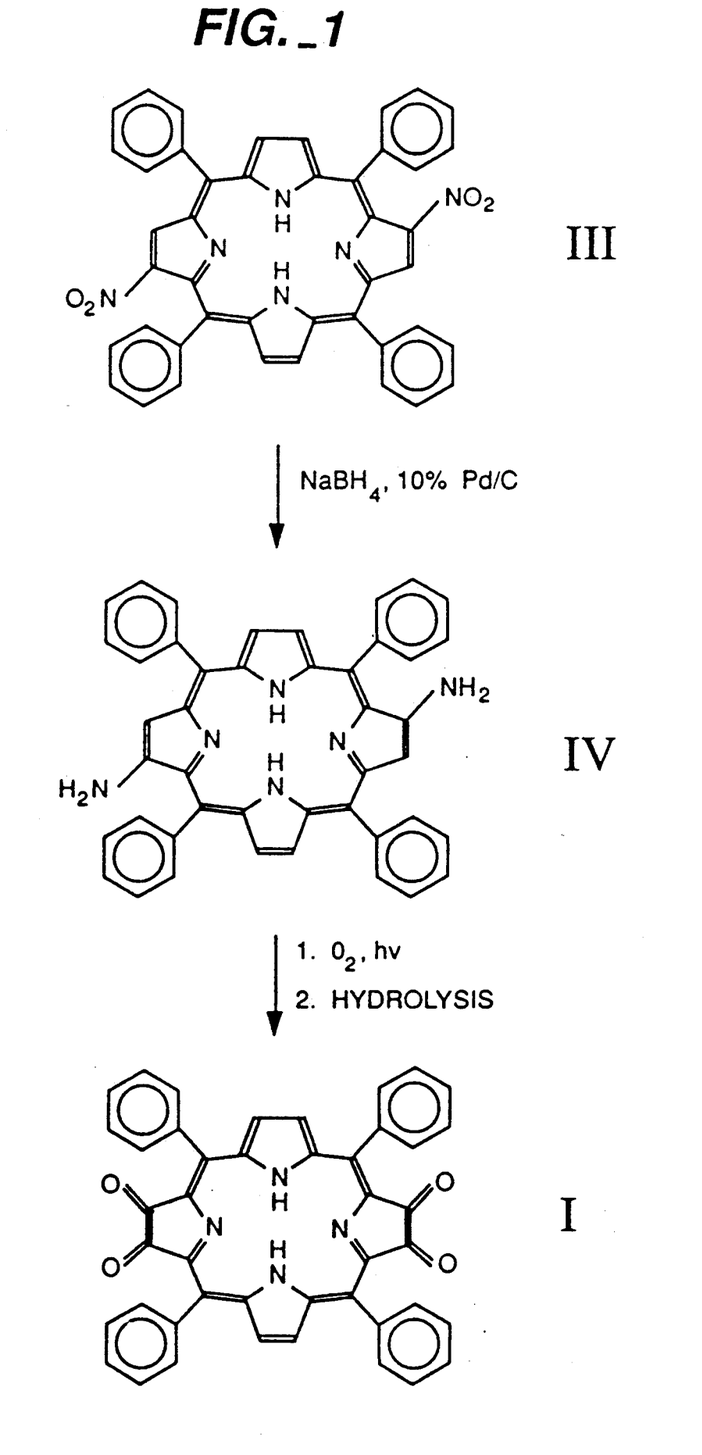
FIG. 1 shows a reaction sequence for the synthesis of a novel tetra-ketoporphyrin (I), where R is phenyl.

Diaminotetraphenylporphyrin—Compound IV: The dinitroporphyrins (Compound III) is dissolved in an aprotic solvent in an inert atmosphere. An alcohol, such as methanol, is added. A catalyst, such as palladium on carbon is added to the Compound IV solution followed by a borohydride reducing agent, such as sodium borohydride. After filtration and removal of the solvent, the crude residue is purified by column chromatography using a polar solvent to produce diamino compound IV.

Tetraketotetraphenylporphyrin—Compound I: Compound IV is dissolved in a aprotic solvent. Oxygen gas is bubbled into the solution which is simultaneously irradiated with tungsten sun lamp. Silica gel is added and stirred at ambient temperature overnight, filtered, and the solvent is removed. Ths solid is redissolved in methylene chloride. Acetic anhydride is added, stirred for 1 day at ambient temperature and washed with aqueous saturated sodium acetate and water, then dried. The solution obtained is purified by chromatography on silica gel using methylene chloride/hexane or benzene/ethyl ether as solvent.

The novel monomer—the tetraketone I where R is phenyl is obtained. NMR and IR spectral analysis are consistent with the tetraketone structure (I) wherein the two alpha diones moieties are not on adjacent porphyrin groups. This result is unexpected.

At the nitration step above, a number of isomers are formed. However, it is found that it is not necessary to separate these isomers. After, the oxidation to form the desired tetraketone I, the isomeric impurities are easily separated by chromatography.

Preparation of Cu(II) Tetraketone (Ia)—Tetraketone I is dissolved in an aprotic solvent and is heated to reflux. Metal acetate (e.g. copper) in alcohol is added and the solution is refluxed under inert gas. The reaction is complete in 3 to 30 hr. After normal workup, the metal containing compound I(a) is obtained. When excess copper or the chloride is used in acetonitrile, an improved yield is obtained.

Figure 5:
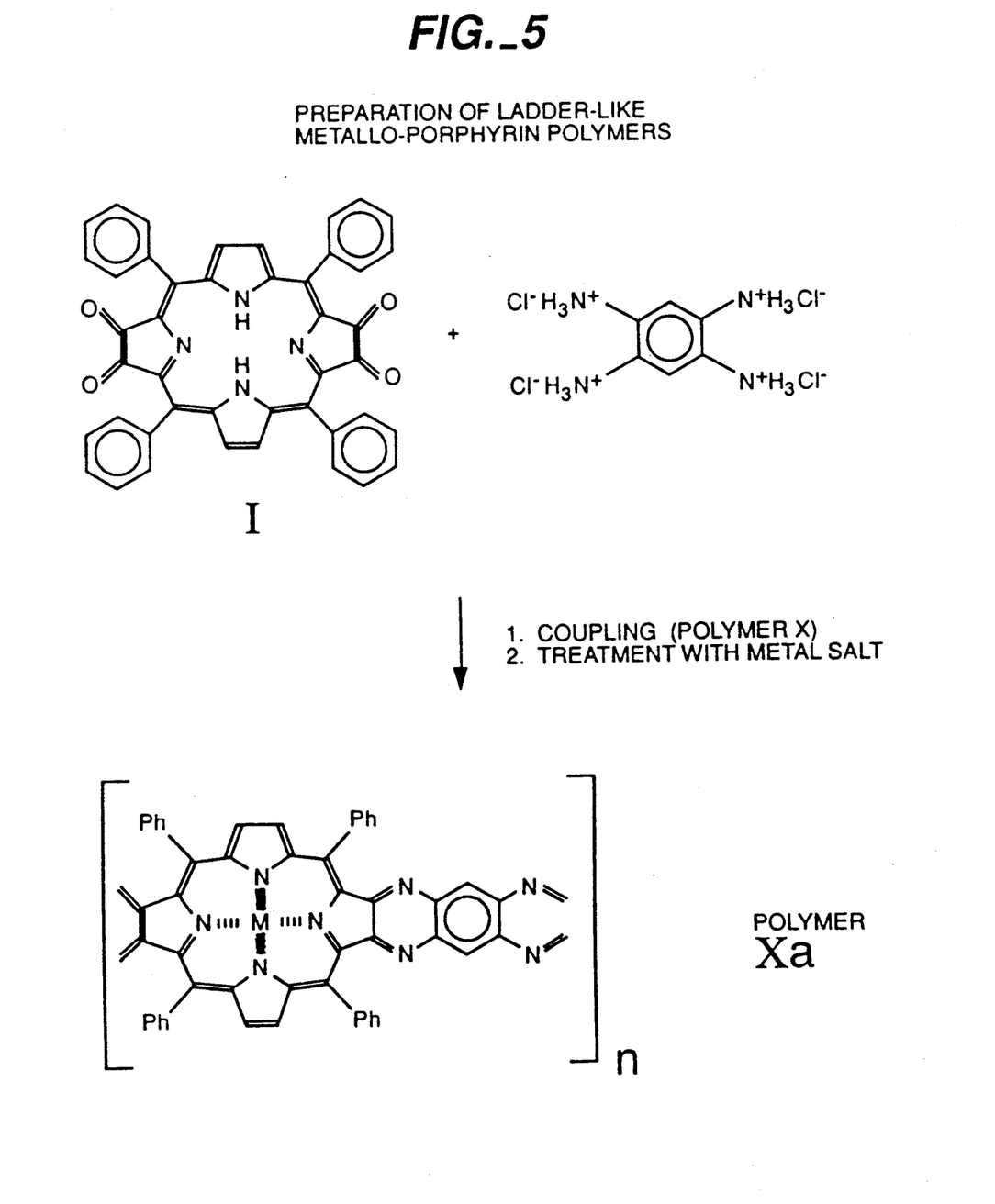
FIG. 5 shows a general reaction for the production of a linear ladder-like metalloporphyrin polymer Xa.

Synthesis of Metal (II) Polymer X—The metal ketone I(a) is dissolved in dipolar aprotic solvent dimethylformamide, and pyridine. The tetraamine —Ar hydrochloride is added. After, 2 days at ambient temperature in the dark, the reaction is complete. The metal containing polymer X(a) is obtained having a mean molecular weight of greater than 10,000 daltons.

Synthesis of Polymer X(a)—The polymer synthesized by condensation of the tetraketone I and tetraamino aromatic compound (Ar) are dissolved in dipolar aprotic solvent and heated to 90°-100° C. under inert gas. Metal (e.g. copper) acetate is added. After 20 hr. at reflux (90°-100° C.), the reaction mixture is cooled. UV-VIS confirmed that the polymer metal (II) complex porphyrin had formed.

The compounds of the structure:

VI are prepared by first treating at least two moles of paradinitrobenzene with one mole of a diol (HO-A-OH) or diol sodium salt in the presence of a base such as potassium tertiary butoxide at about 80° C. for 1 to 4 hours to produce diether VI.

Alternatively, diether VI is prepared by reacting 2 moles of para-nitrophenol with a dihalogen substituted X-A-X where X is Cl, Br or I in the presence of base such as potassium tertiary butoxide.

The coupled product VI is next contacted with excess stannous chloride in about 1 to 2N hydrochloric acid at ambient temperature overnight to produce compound VII.

VII

Compound VII is contacted with a mixture of 70% nitric acid and 0.96% sulfuric acid at about −20° to 0° C. for 1 to 4 hrs. After normal workup, Compound VIII is obtained:

VIII

Compound VIII is contacted again with stannous chloride in 1 to 2N hydrochloric acid at ambient temperature to produce compound of the tetraamine structure desired.

Formation of Linear Porphyrin Polymers—Compound I is contacted with a tetraamine or amine hydrohalide in the presence of a base and a dipolar aprotic solvent in the absence of light in an inert atmosphere. The polymer obtained is subjected to gel permeation chromatography to determine the mean molecular weight of the polymer. Usually a polymer having a molecular weight of about 20,000 daltons or greater (e.g. to about 1,000,000 daltons) is obtained.

These polymers are useful as liquid crystal polymers. Initially, the polymers are evaluated by thermal gravimetric analysis (TGA) and differential scanning calorimetry (DSC). The rheological behavior is studied using a rheometrics mechanical spectrometer.

The electrical conductivity of the polymers is determined by the four-point probe method using cast films. The electrical conductivity was found for the iodine-doped copper (II) polyporphyrin (Xa) was between about 1 and $10 \times 10^{-5}$ ohm$^{-1}$ cm$^{-1}$. The conductivity of the iodine-doped nickel (II) polyporphyrin (Xa) was between about 1 and $10 \times 10^{-4}$ ohm$^{-1}$ cm$^{-1}$. The conductivity of polyporphyrin (X) without metal was about $1.34 \times 10^{-4}$ ohm$^{-1}$ cm$^{-1}$. It is expected that these and the other polyporphyrin polymers described herein, including the described metal ions, will exhibit an electrical conductivity of between about $1 \times 10^{-4}$ to $10^{-5}$ ohm$^{-1}$ cm$^{-1}$.

Changes in UV-visible spectra of the polymers with applied potential are determined by casting polymer films on indium-tin oxide (ITO), platinum or gold-coated semitransparent electrodes. Reversibility and response time are determined as is described in published methods.

The materials, chemicals or reagents for the present invention are commercially available from chemical supply houses such as Aldrich Chemical Company of Milwaukee, Wis. Other suppliers can be located in *Chem Sources, U.S.A.*, which is published annually by Directories Publishing, Inc. of Clemson, S.C. The chemicals are usually used without further purification unless otherwise noted.

The following Examples are presented to be illustrative and explanatory only. They are not to be construed as limiting in any way.

EXAMPLE 1

Tetraphenylporphyrin (II)

(a) The preparation of (II) is accomplished according to the procedure described by A. D. Adler et al., *Journal of Organic Chemistry*, Vol. 32, (1967) 476, which is incorporated herein by reference. This procedure uses pyrrole and benzaldehyde in acetic or propionic acid solution. (FIG. 2).

(b) The reaction of Example 1(a) is repeated except that benzaldehyde is replaced with a stoichiometrically equivalent amount of 4-methylbenzaldehyde. The corresponding tetra(4-methylphenyl)porphyrin is obtained.

EXAMPLE 2

Copper (II) Tetraphenylporphyrin (IIa)

Tetraphenylporphyrin (II) (16.80 g., 27.3 mmol) is dissolved in 2000 ml of chloroform under reflux. Copper (II) acetate monohydrate (5.45 g., 27.3 mmol) is dissolved in 600 ml of methanol, and added dropwise to the methylene chloride solution in about 15 minutes. After the addition is over, the solution is refluxed for 30 minutes and cooled. The completion of the reaction is checked by UV-VIS spectrophotometry. The product IIa is isolated by evaporation of the solvents.

The reaction of Example 2(a) is repeated except that the copper (II) acetate is replaced with a stoichiometrically equivalent amount of iron (II) nitrate. The corresponding iron (II) porphyrin is produced.

EXAMPLE 3

Copper (II) Dinitrotetraphenylporphyrin (IIIa)

(a) Copper (II) tetraphenylporphyrin (IIa) (2.0 g., 2.96 mmol) is dissolved in 300 ml of anhydrous methylene chloride under a nitrogen blanket The solution is a dark red color.

In a glass cylinder 3.37 g. of dinitrogen tetraoxide ($N_2O_4$) are transferred, and anhydrous methylene chloride is added until the total volume is 20 ml. 3.4 Ml of the methylene chloride solution are transferred by a double tip needle to an addition funnel and dropped into the methylene chloride solution of compound IIa. In a few minutes after the addition of $N_2O_4$ is complete, the reaction solution turns green. The reaction progress is checked by thin layer chromatography after 30 min. A principle product III(a) is present. The UV-VIS spectrum of the crude reaction shows strong absorbance at 432 nanometer (nm).

EXAMPLE 4

Dinitrotetraphenylporphyrins (IIIa)

(a) The crude Compound IIIa (22.23 g) is dissolved in methylene chloride (800 ml). To this solution is added 100 ml of sulfuric acid (96%), and the mixture is stirred for 15-20 minutes. Next, the reaction mixture is poured into ice-water, the aqueous layer is extracted several times with methylene chloride. The organic layer and washes are washed with water and 5% sodium bicarbonate, and dried over magnesium sulfate. FT IR shows absorption at 1510 cm$^{-1}$ and 1340 cm$^{-1}$; ($-NO_2$ asymmetrical and symmetrical stretching). Mass spectrometry (field ionization) showed essentially Compound III; m/e=704. Other isomers are present.

EXAMPLE 5

Diaminotetraphenylporohyrin IV

Compound III 800 mg (1.14 mmol) is dissolved in 200 ml of methylene chloride under argon. Methanol (50 ml) is added, and the solution remains homogeneous. Palladium (10%) on carbon (1.96 g.) added, followed by solid sodium borohydride (2.08) g., 54 mmol) is added in small portions over about 15 min. The solution, which first turns to red then to red-brown, is stirred for about 40 min. Anhydrous methylene chloride (200 ml) is added, and the solution is filtered through Celite. The filtrate is removed under reduced pressure. The residue is stirred with 200 ml of anhydrous methylene chloride and filtered again. The filtrate is concentrated again using reduced pressure, and the crude residue, about 1 g., is recovered. The diaminoporphyrins are purified by flash chromatography on silica gel using methylene chloride as eluent. The infrared, the proton magnetic resonance and mass spectra are consistent with the diamino structure IV.

EXAMPLE 6

Tetraketotetraphenylporphyrin (I)

(a) To a 300 ml flask are added the diaminotetraphenylporphyrin isomers IV (200 mg) and 80 ml of methylene chloride (anhydrous). Oxygen is bubbled into the solution which is irradiated with a solar lamp. The reaction progress is monitored by TLC (silica gel). The eluent is methylene chloride or methylene chloride/hexane (7/3:v/v). From the TLC, after 4 hr., the diamino compounds IV appear to have been completely converted. The methylene chloride solution is stirred overnight with 1 g. silica gel in air. The tetraketotetraphenyl-porphyrin (I) is isolated from the oxide product by preparative, centrifugally accelerated, thin layer chromatography, using a rotor coated by a silica gel layer 4 mm. thick and benzene/1% ethyl ether as eluent. The spectroscopic analysis (VIS, IR, $^1$H-NMR) are consistent with the attribution of the structure (I).

(b) The diaminotetraphenylprophyrins (350 mg) were dissolved in anhydrous methylene chloride (350 mL) and transferred into a round bottom three neck flask equipped with an oxygen inlet and reflux condenser. The reaction solution was photoexposed to two 250 watt bulbs, and oxygen was bubbled through. The reaction was monitored by TLC. After six hours, the irradiation and the oxygen purge were suspended, since no more starting materials were seen by TLC. Silica gel was then added to the solution, and the mixture was stirred at room temperature over night. After this time, the solution was filtered and the solvent distilled under reduced pressure to give the photo-oxidized crude products (250 mg. The solid (250 mg.) obtained from the hydrolysis of the photo-oxidized diamino tetraphenylporphyrins was redissolved in methylene chloride (5 mL). Acetic anhydride (2.5 mL) was added to the solution. The solution was stirred for twenty-four hours at room temperature. It was then washed three times with saturated aqueous solution of sodium acetate (10 mL) and then twice with water (10 mL). The solution was dried over anhydrous sodium sulfate for two hours. The residue was then chromatographed on silica gel (eluent benzene or methylene chloride). The second green fraction (tetraketone) was collected and crystallized from methylene chloride hexane (yield 50 mg.).

EXAMPLE 7

Polymerization of Tetraketotetraphenyl—Porphyrin I and A Tetraaminotetrahydrochloride (a) Compound I (8.5 mg., 0.0130 mmol) and 1, 2, 4, 5-tetraaminobenzene tetrahydrochloride (3.73 mg., 0.0131 mmol), dimethylformamide (1 ml) and pyridine (0.5 ml) are combined producing a homogeneous solution which is kept under an argon blanket in the dark at ambient temperature. After 112 hr., the solvent is distilled off under vacuum and the linear ladder polymer is isolated. The polymer is characterized by gel permeation chromatography (gpc). The portion of polymer soluble in dimethyformamide has a molecular weight of about 20,000 to 2,400,000 daltons, or greater computed against monodispersed polystyrene calibration standards. The remaining portion is insoluble in the characterization solvent and therefore has higher molecular weight.

The polymer structure was consistent with this structure by gel permeation chromatography, infrared spectral analysis, thermal gravimetric analysis and differential scanning calorimetry (b) The polymerization reaction of Example 7(a) is repeated except that the tetraaminobenzenetetrahydrochloride is replaced by:
3, 4, 3', 4'-tetraaminobiphenyl;
3, 4, 3', 4'-tetraaminobiphenyloxide;
3, 4, 3', 4'-tetraaminobiphenysulfide;
3, 4, 3', 4'-tetraaminobiphenylsulfone;
3, 4, 3', 4'-tetraaminobiphenysulfoxide;
3, 4, 3', 4'-tetraaminobiphenylazine;
2, 3, 6, 7-tetraaminonaphthalene;
1, 2, 5, 6-tetraaminonaphthalene;
1, 4, 5, 8-tetraaminonaphthalene;
2, 3, 7, 8-tetraaminoanthracene;
1, 2, 6, 7-tetraaminoanthracene;
1, 4, 5, 10-tetraaminoanthracene;
1, 5, 6, 10-tetraaminoanthracene;
2, 3, 7, 8-tetraaminoanthracene;

wherein when Q is oxygen (O), A is selected from —(CH$_2$)$_m$—; —(CF$_2$)$_m$—; —(CF$_2$CF(CF$_3$))$_m$—, —(CH$_2$CH)$_m$—; or when Q is a direct carbon-carbon bond, A is selected from —(CH$_2$CH$_2$O)$_m$—, —(CH$_2$CH(CH$_3$))$_m$, —(CF$_2$CF(CF$_3$)O)$_m$—, or —(Si(R$_2$)O)$_m$—, wherein R' is methyl, ethyl, propyl, butyl or phenyl, and m is between about 1 and 10,000, wherein each of the above tetraamines are present as the tetrahydrogen chloride.

EXAMPLE 8

Preparation of Cu(II) Tetraketone

The tetraketone (30 mg., 4.45. mmol) is dissolved in chloroform (5.0 ml) and the solution is reflux. To the solution is added copper acetate in methanol dropwise (10 mg. in 2.0 ml of methanol). The reaction mixture is refluxed under nitrogen. The copper complexation is followed by UV-VIS spectroscopy, by monitoring the shift of the lambda max from 384 nm. to 418 nm. After 20 hours the conversion is complete. The solvents are evaporated under vacuum, the residue is dissolved in methylene chloride and washed with water. The organic layer is dried over MgSO$_4$, and the product, I(a), is recovered by evaporation of the solvent. The structure is consistent with infrared spectral analysis and mess spectral analysis. When excess copper as the chloride is used, an improved yield is obtained.

EXAMPLE 9

Synthesis of the Cu(II) Polymer

The Cu(II) tetraketone (20 mg., 0.027 mmol) is dissolved in 2-ml of dimethylformamide and 1-ml of pyridine. To this solution 1,2,4,5-benzenetetraamine tetrahydrochloride (7.72 mg., 0.027 mmol) is added. The solution is stirred in the dark, under nitrogen for 2 days, By gel permeation chromatography (gpc) a polymer with molecular weight 15,000 daltons is detected. The structure was consistent by gel permeation chromatography.

EXAMPLE 10

Preparation of Cu(II) Polymer

The polymer is synthesized by condensation of the tetraketone with 1,2,4,5 -benzenetetraamine tetrahydrochloride (5 mg.) is dissolved in 2.0 ml. of dimethylformamide and heated up to 90°-100° C. under nitrogen. To this solution, copper acetate is added (10 mg. in 1.0 ml of dimethylformamide). The reaction solution is held at 90°-100° C. for 20 hours. The formation of the Cu(II) complex of the polymer is verified by a change in the UV-VIS spectrum of the compound in dimethylformamide. The product was consistent by thermal gravimetric analysis and differential scanning calorimetry.

In the polymerization of the monomers to obtain Polymer X (no metal present) or Polymer Xa (metal present), n is the degree of polymerization. "n" is between about 2 and 3000, preferably between about 4 and 2000, and most preferably between about 5 and 100. "n" is especially preferred between 5 and 20.

EXAMPLE 11

Electrical Conductivity Measurements

Electrical conductivity measurements were determined on a pressed polymer pellet by the four-point probe method and by applying a.c. voltage through stainless-steel electrodes. The polymers were somewhat crumbly.

(a) Iodine-doped copper (II) polyporphyrin (Xa) showed a conductivity of $3.33 \times 10^{-5}$ ohm$^{-1}$ cm$^{-1}$. A 0.0122-cm-thick polymer pellet was prepared under a pressure of 12,000 psi. The pellet was doped with iodine by exposing the pellet to iodine vapors for 24 hours at 50° C.

(b) Iodine-doped nickel (II) polyporphyrin (Xa) showed a conductivity of $2.23 \times 10^{-4}$ ohm$^{-1}$ cm$^{-1}$. A polymer pellet 0.0142 cm thick was fabricated making by using a press. The pellet was doped by exposure to iodine vapor for about 15 hours at 60° C.

(c) Copper (II) poly(porphyrin) was also doped with nitrosonium tetrafluoroborate by stirring the polymer powder in a chloroform solution of the doping agent at room temperature overnight. The polymer was then washed with chloroform and a pellet was prepared. The polymer conductivity was determined by impedance measurements on stainless steel electrodes. The impedance spectra were recorded in the frequency range 13 Mhz to 5 Hz on a 4192A LF Hewlett-Packard Frequency Analyzer. A conductivity of $6.2 \times 10^{-6}$ ohm$^{-1}$ cm$^{-1}$ was determined.

(d) Following the analogous procedure, an electrical conductivity of $1.34 \times 10^{-4}$ ohm$^{-1}$ cm$^{-1}$ was determined for the polyporphyrin (X) without any metal ion present.

EXAMPLE 12

Non-Linear Optical Properties

For the evaluation of the third non-linear optical property, the third order susceptibility tensor value, $X^{(3)}$ of the polyporphyrin prepared by condensation of tetraketone with 1,2,4,5-benzene tetraamine were determined as $1 \times 10^{-11}$ esu, by the method of degenerate four-wave mixing.

Measurements of the third order susceptibility tensor, $X^{(3)}$, in the polymer and a variety of solvents were made using the method of degenerate four-wave mixing (DFWM), a technique from which the fast non-linear response of a material may be characterized from its phase conjugate reflectivity. The experiment was performed in the picosecond regime with a mode-locked Nd:YAG-pumped tunable dye laser operating at 645 nm with a 5 picosecond pulsewidth. The output of the dye laser was subsequently passed through a series of three dye amplifier stages, where pulse energies on the order of a few hundred microjoules were obtained. The output of the amplifier chain was then directed through a variable attenuator and into the DFWM apparatus.

Degenerate four-wave mixing was attained by splitting the amplified beam into three components: a weak probe, designated here as $I_3$, and two strong pump beams, $I_1$ and $I_2$. After travelling through computer-controlled optical delay lines, all three beams were focussed into the samples in the anti-resonant ring geometry. This involved counterpropagating the two strong pump beams against each other through the sample and overlapping the weak probe with the pump-irradiated sample volume. When all three timed to arrive at the sample simultaneously, a fourth beam, $I_4$, the complex phase of conjugate of $I_3$, evolved and travelled back along $I_3$, where it could be picked off and detected. In order to separate the fast electronic nonlinear response of the material from slower, thermal grating effects, the polarization of $I_3$ was rotated 90° before entering the sample.

Measurements of a sample's phase conjugate reflectivity versus pump intensity were made using photodiode detectors to monitor pump and phase conjugate intensities on a single shot-correlated basis. Signals from the photodiodes were processed through boxcar integrators and A/D converters, and recorded by computer as the energy delivered to the sample was varied using the attenuator.

The polymer sample was dissolved in dimethylformamide (DMF) and sandwiched between two quartz windows to achieve a thickness of roughly 125 microns. In the same cell and adjacent to the polymer was a sample of pure dimethylformamide (DMF). The phase conjugate reflectivity was then measured and compared directly that of pure DMF. Allowing for absorption losses, the phase conjugate reflectivity of the sample measured to be 1.9 times that of the DMF. With the amount of dilution used in this trial, the $X^{(3)}$ of the polymer is calculated to be 950 times that of DMF. From earlier comparisons of the picosecond values of $X^{(3)}$ for DMF and carbon disulfide (CS$_2$), a well-characterized standard, there is obtained a preliminary value of $X^{(3)}$ for the polymer of approximately $1 \times 10^{-11}$ esu.

While only a few embodiments of the invention have been shown and described herein, it will become apparent to those skilled in the art that various modifications or changes can be made in the process to produce tetraketoporphyrins and the porphyrin-based metal polymers thereof without departing from the spirit and scope of the present invention. All such modifications and changes coming within the scope of the appended claims are intended to be carried out thereby.

We claim:

1. A polymer of the structure:

wherein
M is a metal atom;

R is selected from phenyl, alkyl substituted phenyl, halogen substituted phenyl and alkoxy substituted phenyl; and

Ar is selected from the group consisting of:

where when Q is oxygen, (O), A is —$(CH_2)_m$—, —$(CH_2CH(CH_3))_m$—,

—$(OCF_2CF_2)_m$—, or —$(CF_2—CF(CF_3))_m$—, where m is 1 to 10,000; or when Q is a direct carbon-carbon bond, A is —$(CH_2CH_2O)_m$—, —$(CH_2CH(CH_3)O)_m$—, or —$(SiR'_2O)_m$—, wherein R' is methyl, ethyl, propyl, or butyl and m is 1 to 10,000; and n is between 2 and 3000.

2. A process to produce a linear polymer of the structure:

X or

Xa wherein M is a metal atom; n is between 2 and 3000;

Ar is an organic moiety having two separate sets of two adjacent reaction sites contained in at least one aromatic ring;

R is selected from phenyl, alkyl substituted phenyl, or halogen substituted phenyl, which process comprises:

(a) contacting a tetraketone of structure:

(I)

with a tetraamine or a tetraamine hydrohalide of one organic moiety having two separate sets of adjacent reaction sites containing at least one aromatic ring;

(b) maintaining the solution of step (a) in the presence of a strong organic base and a dipolar aprotic solvent for between about 1 and 10 hr. at about ambient temperature; and recovering the polymer of structure X; and

(c) optionally adding a metal M salt to produce structure Xa.

3. The process of claim 2 wherein the tetraamine is selected from the group consisting of:

or or wherein when Q is oxygen (O), A is $(-CH_2)_m-$, $-(CH_2CH(CH_3))_m-$, $-(OCF_2CF_2)_m-$, or $-(CF_2-CF(CF_3))_m-$, and m is between 1 and 10,000; or when Q is a direct carbon-carbon bond, A is $-(CH_2CH_2O)_m-$, $-(CH_2CH(CH_3)O)_m-$, or $-(SiR'_2O)_m-$, wherein R' is methyl, ethyl, propyl, or butyl, and m is between 1 to 10,000, and n is between 2 and 3000, or the tetrahydrohalides thereof.

4. The process of claim 2 wherein the tetraamine is selected from:

5. The process of claim 2 which further includes treatment with a metal salt M to form the metal containing porphyrin polymer Xa:

6. The polymer of structure X:

wherein
R is selected from phenyl, alkyl substituted phenyl, halogen substituted phenyl and alkoxy substituted phenyl; and
Ar is selected from the group consisting of:

p1 wherein when Q is oxygen (O), A is $-(CH_2)_m-$, $-(CH_2CH(CH_3))_m-$, $-(CH_2-CH)_m-$,
       |
     (phenyl)

$-(OCF_2CF_2)_m-$, or $-(CF_2-CF(CF_3))_m-$, where m is 1 to 10,000; or when Q is a direct carbon-carbon bond, A is —(CH$_2$CH$_2$O)$_m$—, —(CH$_2$CH(CH$_3$)O)$_m$—, or —(SiR'$_2$O)$_m$—, wherein R' is methyl, ethyl, propyl, or butyl and m is 1 to 10,000; and n is between 2 and 3000.

7. The polymer of claim 6 wherein R is phenyl.

8. The polymer of claim 7 wherein Ar is

9. The polymer of claim 7 wherein Ar is

10. The polymer of claim 7 wherein M is copper.

11. The process of claim 3 wherein M is selected from copper, iron, cobalt, nickel or manganese.

12. The process of claim 11 wherein R is phenyl.

13. The polymer produced by the process of claim 3 wherein the polymer is electrically conducting.

14. The polymer of claim 8 wherein the polymer is electrically conducting.

15. The polymer produced by the process of claim 4.

16. The electrically conducting polymer produced by the process of claim 2 wherein the conductivity is between about $1 \times 10^{-4}$ and $1 \times 10^{-5}$ ohm$^{-1}$ and cm$^{-1}$.

17. The electrically conducting polymer produced by the process of claim 2 wherein the polymer has the structure of the product of the reaction of the tetraphenyl tetraketone (I) and 1,2,4,5-tetra-aminobenzene, and the metal is copper.

18. The electrically conducting polymer of claim 17 which is doped with idoine.

19. The electrically conducting polymer of claim 17 wherein the polymer is doped with nitrosonium tetrafluoroborate.

20. The electrically conducting polymer produced by the process of claim 2 wherein the polymer has the structure of the product of the reaction of tetra phenyl tetra ketone (I) and 1,2,4,5-tetraamino-benzene, and the metal is nickel.

21. The electrically conducting polymer of claim 17 wherein the polymer is doped with iodine.

22. The electrically conducting polymer of claim 18 having a conductivity of about $3.3 \times 10^{-5}$ ohm$^{-1}$cm$^{-1}$.

23. The electrically conducting polymer of claim 19 having a conductivity of about $6.2 \times 10^{-6}$ ohm$^{-1}$cm$^{-1}$.

24. The electrically conducting polymer of claim 21 having a conductivity of about $2.2 \times 10^{-4}$ ohm$^{-1}$cm$^{-1}$.

25. The polymer of claim 6 wherein R is phenyl, and n is between 2 and 2000.

* * * * *